US00PP35400P2

(12) United States Plant Patent
Read

(10) Patent No.: US PP35,400 P2
(45) Date of Patent: Sep. 26, 2023

(54) ***LEUCANTHEMUM* PLANT NAMED 'REAL CREAM'**

(50) Latin Name: ***Leucanthemum* x *superbum***
Varietal Denomination: Real Cream

(71) Applicant: Charles Richard Read, Bognor Regis (GB)

(72) Inventor: Charles Richard Read, Bognor Regis (GB)

( * ) Notice: Subject to any disclaimer, the term of this patent is extended or adjusted under 35 U.S.C. 154(b) by 0 days.

(21) Appl. No.: 18/066,058

(22) Filed: Dec. 14, 2022

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./284, 285
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A new cultivar of *Leucanthemum* plant named 'Real Cream' that is distinguishable by its vigorous basal-branching upright plant habit, long, narrow dentate foliage, and inflorescences consisting of three whorls of overlapping ray florets. The ray florets of 'Real Cream' are yellow in color when first opening, becoming soft cream in color when fully expanded. The inflorescences of 'Real Cream' are carried on a strong stiff stems and are long-lasting and suitable for use as cut flowers. 'Real Cream' flowers in mid-summer and re-flowers in the fall. 'Real Cream' is hardy in USDA Zone 5.

2 Drawing Sheets

Genus and species: *Leucanthemum* x *superbum.*
Variety denomination: 'Real Cream'.

BACKGROUND OF THE NEW PLANT

The present invention relates to a new and distinct cultivar of *Leucanthemum* commonly known as Shasta daisy, which is grown as an ornamental plant for use in the garden and landscape. The new cultivar is known botanically as *Leucanthemum* x *superbum* and will be referred to hereinafter by the cultivar name 'Real Cream'.

*Leucanthemum* is a genus within the family Asteraceae in which the commonly referred to "flower" is botanically the inflorescence which is comprised of outer showy ray florets surrounding smaller disc florets.

'Real Cream' arose and was selected from an ongoing breeding program which is conducted by the inventor at the inventor's nursery in West Sussex, United Kingdom. The breeding program commenced in 2006 with the aim of developing new and improved commercial varieties of *Leucanthemum*. Each year's breeding cycle consists of controlled pollination between chosen male and female parents including unnamed and unreleased seedlings retained from previous breeding cycles. Seed from each year's cycle is harvested and sown in the fall, and new seedlings are raised and evaluated in the following summer.

'Real Cream' is a seedling selection that resulted from the controlled pollination in of a single plant of the inventor's proprietary *Leucanthemum* seedling code L1403-12 (unreleased and unpatented) as the female parent, using pollen from a single plant of the inventor's proprietary *Leucanthemum* seedling code L1329-7 (unreleased and unpatented) as the male parent. The inventor selected 'Real Cream' in 2017 for its combination of vigorous basal branching, uniformly narrow foliage, and inflorescences which are yellow in bud and which open as whorls of overlapping cream-yellow ray florets.

'Real Cream' was first asexually propagated by the inventor in West Sussex, United Kingdom in 2020 using the method of vegetative division and subsequently by basal shoot cuttings. Since that time under careful observation 'Real Cream' has been determined uniform, stable and true to type in subsequent generations of asexual propagation.

SUMMARY

The following traits have been repeatedly observed and represent the distinguishing characteristics of 'Real Cream'. In combination, these traits set 'Real Cream' apart from all other existing varieties of *Leucanthemum* known to the inventor. 'Real Cream' has not been tested under all possible conditions and phenotypic differences may be observed with variations in environmental, climatic, and cultural conditions, however, without any variance in genotype.

1. 'Real Cream' exhibits vigorous basal-branching and upright plant habit.
2. The leaves of 'Real Cream' are uniformly long and narrow and have prominent dentate margins.
3. A fully expanded inflorescence of 'Real Cream' is 7.0-7.5 cm in diameter and is comprised of cream-yellow ray florets arranged around a dark yellow central disc.
4. The ray florets of 'Real Cream' are arranged in three concentric whorls with overlapping ray floret petals.
5. The ray florets of 'Real Cream' are yellow in color when first opening, becoming soft cream in color when fully expanded.
6. The inflorescences of 'Real Cream' are carried on a strong stiff stems and are long-lasting and suitable for use as cut flowers.

7. 'Real Cream' flowers in mid-summer and reflowers in the fall.
8. 'Real Cream' is hardy in USDA Zone 5 (−20° F. or −28° C.).

BRIEF DESCRIPTION OF THE PHOTOGRAPHS

The accompanying color photographs were taken in July 2022 in Santa Barbara, Calif. The photographs illustrate the overall appearance of 'Real Cream' showing the color of foliage and inflorescence as true as is reasonably possible to obtain in color reproductions of this type. The illustrated plants had been grown in 2-gallon containers out of doors, without any pruning or use of chemical growth regulators. The colors in the photographs may differ from color values cited in the detailed botanical description, which accurately describe the actual color of 'Real Cream'.

BOTANICAL DESCRIPTION OF THE PLANT

Figure 1:
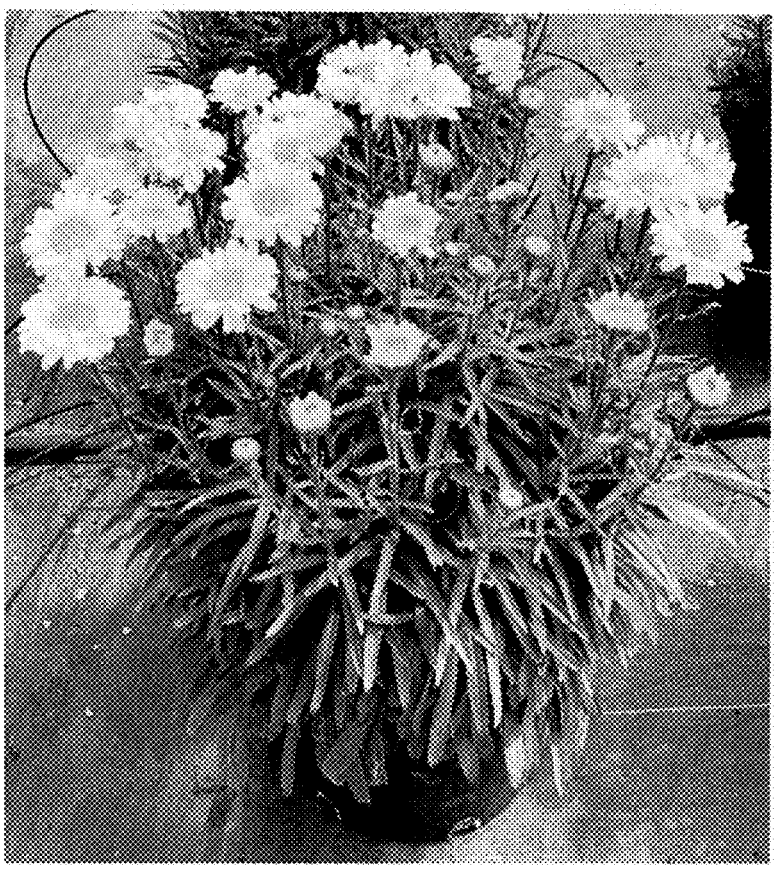
FIG. 1 illustrates, in the foreground, an eighteen month old plant of 'Real Cream' (from initial cuttings) which is growing outdoors in a 2-gallon container.
Figure 2:
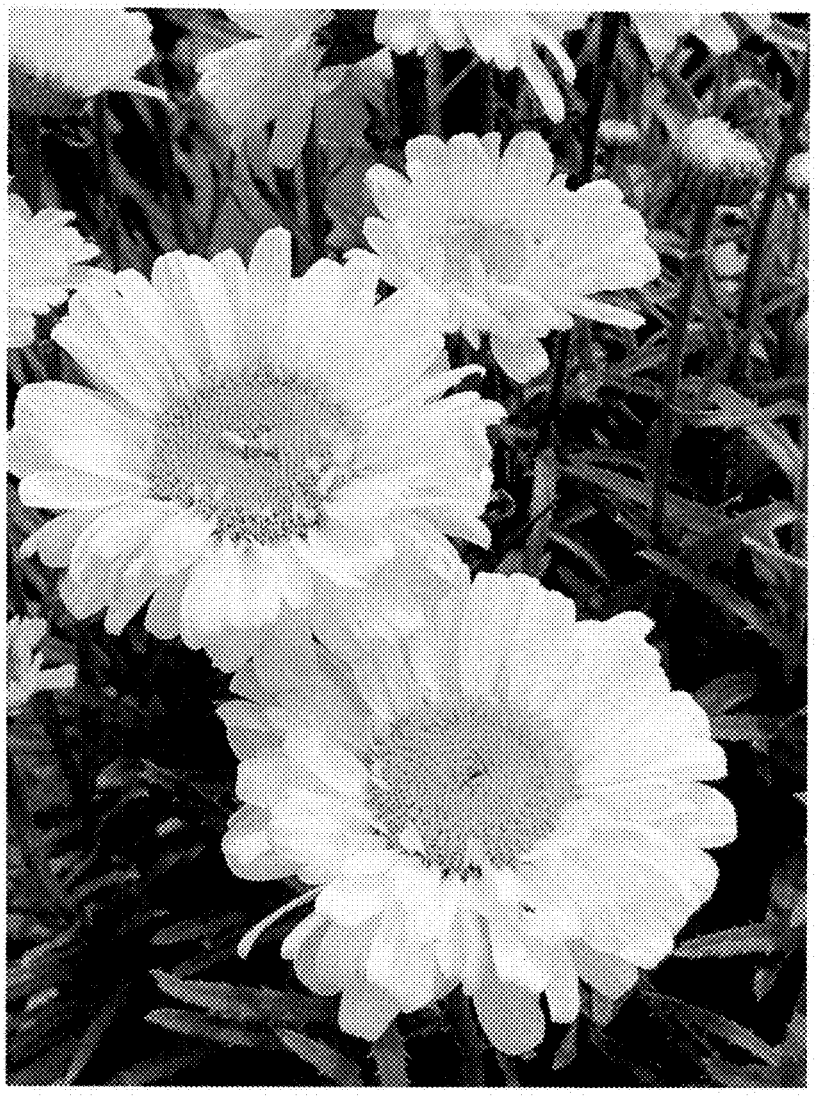
FIG. 2 depicts a close-up view of the inflorescences of 'Real Cream'.

The following is a detailed botanical description of the new cultivar 'Real Cream'. Observations, measurements, values and comparisons were collected in Santa Barbara, Calif. during August 2022, from an eighteen months old plant growing outdoors in 2-gallon container. Color determinations are made in accordance with The 2007 Royal Horticultural Society Colour Chart from London, England, except where general color terms of ordinary dictionary significance are used.

Botanical classification:

*Family*.—Asteraceae (formerly Compositae).

*Genus*.—*Leucanthemum*.

*Species*.—x *superbum*.

*Denomination*.—'Real Cream'.

*Common name*.—Shasta daisy

*Habit*.—Vigorous basal-branching and upright growth habit.

*Commercial category*.—Perennial.

*Use*.—For garden and landscape.

*Suggested commercial container size*.—4-inch, 1 gallon, 2-gallon containers.

*Parentage*.—*Leucanthemum* x *superbum* 'Real Cream' is a seedling selection resulting from the controlled cross-pollination of the following parents — Male parent: inventor's proprietary *Leucanthemum* seedling code L1329-7. Female parent: inventor's proprietary *Leucanthemum* seedling code L1403-12.

*Propagation method*.—Basal shoot cuttings and division.

*Rooting system*.—Fine and fibrous.

*Vigor*.—Vigorous

*Time to develop roots* (*range*).—14 to 20 days are needed for an initial cutting to develop roots.

*Temperature to develop roots* (*range*).—The recommended air temperature is 20° C. to 21° C.

*Crop time* (*range*).—7 to 8 months to produce a flowering plant in a 1-gallon container starting from a rooted cutting. 10 months to produce a full plant in a 2-gallon container.

*Plant dimensions* (*eighteen months*).—40 cm in height and 35 cm in width.

*Cultural requirements*.—Grow in full sun and rich, moist moderately fertile well-draining soil.

*Pest or disease resistance and susceptibility*.—No specific disease or pest resistance or susceptibility has been observed or is known to the inventor.

*Hardiness*.—USDA Zone 5.

Stems, branches:

*Description*.—Plant is pinched or stopped at first node close to soil level which encourages vigorous basal branching. Lateral branches borne on basal branches. All basal and lateral stems bear terminal inflorescences.

*Original stem below first pinch or stop*.—Shape: Short cylindrical. Dimensions: 1-2 cm in length, 1 cm in diameter. Surface: Lignified, rough, color 197B.

*Basal stems and lateral stems*.—Shape: Terete. Dimensions: 30-35 cm in length (base to calyx), 7 mm in diameter towards base, 4-5 mm in diameter immediately below calyx. Color: 137C. Surface: Pubescent, hairs 1.0-1.5 mm in length, fine, color NN155D. Strength: Rigid towards base, stiff, wiry towards apex.

Foliage:

*Type* (*division*).—Simple.

*Arrangement*.—Alternate.

*Internode distance*.—1 cm. (average).

*Margin*.—Puberulent (except teeth), dentate, teeth approximately 1 cm apart, prominent, length (beyond leaf margin) up to 4 mm, width at base, 1.0-1.5 mm, aspect pointing towards leaf apex, teeth margin glabrous.

*Apex*.—Acute.

*Base*.—Cuneate.

*Leaf attachment*.—Sessile.

*Leaf color* (*adaxial surface*).—137A.

*Leaf color* (*abaxial surface*).—137D.

*Leaf shape*.—Narrowly lanceolate, almost linear.

*Leaf dimensions*.—9.5 cm in length, 1.5 cm in width.

*Leaf venation*.—Pinnate branching from midrib, then longitudinally parallel.

*Vein color* (*both surfaces*).—137C.

*Leaf surface* (*adaxial surface*).—Glabrous, semi-glossy.

*Leaf surface* (*abaxial surface*).—Puberulent overall, pubescent midrib, hairs short, fine color NN155D.

Inflorescence:

*Inflorescence type*.—Capitulum, flattened dome, consisting of ray florets and disc florets.

*Inflorescence quantity* (*average*).—30 (including colored buds).

*Inflorescence diameter* (*fully opened*).—7.0-7.5 cm.

*Inflorescence height* (*including calyx*).—2.5 cm.

*Inflorescence aspect*.—Upright.

*Inflorescence colors*.—Ray flowers on emergence: 4A. Ray flowers when fully developed: Between 155A and 2D. Central disc: 14A.

*Blooming season*.—Early-mid summer, reflowers in the fall.

*Lastingness of inflorescence, persistence*.—10-14 days on or off the plant, ray florets are persistent.

Bud:

*Bud dimensions*.—8 mm in height and 13 mm in diameter.

*Bud shape*.—Flattened sphere.

*Bud color.*—147B, flattened apex striped (margins of involucral bracts), 183A.
*Bud surface.*—Glabrous.

Peduncle:
*Peduncle shape.*—Terete.
*Peduncle length (from uppermost leaf to base of calyx).*—6.5 cm to 7.0 cm.
*Peduncle diameter.*—3.0 mm to 3.5 mm.
*Peduncle surface.*—Pubescent, hairs 1.0-1.5 mm in length, fine, color NN155D.
*Peduncle strength.*—Strong and wiry.
*Peduncle color.*—137C.

Peduncle bracts:
*Arrangement, quantity.*—One single bract attached 2-4 cm. below calyx; one or two bracts attached immediately below calyx.
*Attachment.*—Sessile.
*Shape.*—Lanceolate but contorted (twisted).
*Margin.*—Minutely dentate.
*Apex.*—Acute.
*Base.*—Truncate.
*Color (both surfaces).*—137A.
*Dimensions.*—Single bract 2-4 cm below calyx: 25 mm in length, 5 mm in width. Bracts at base of calyx: 5 mm in length, 2.5 mm in width.
*Surface (both surfaces).*—Glabrous.

Ray florets:
*Ray floret arrangement.*—Whorled, consisting of three concentric whorls of broad strap-like ray florets. Occasionally, an inflorescence may consist of two full whorls and the third whorl carries a reduced number of ray florets.
*Shape.*—Ligules broadly lanceolate.
*Quantity.*—65-75 per inflorescence.
*Aspect.*—Emerge upward-facing becoming horizontal when fully open.
*Corolla tube dimensions.*—4 mm-5 mm in length, 1 mm in diameter.
*Corolla tube color.*—143C.

Ray floret petals:
*Shape.*—Strap-like, longitudinally furrowed, average 5 furrows or ridges 1.5-2.0 mm apart.
*Arrangement.*—Overlapping.
*Surface (both surfaces).*—Glabrous.
*Apex.*—Truncate, apex margin color 8B.
*Base.*—Attenuate.
*Margin.*—Entire.
*Dimensions.*—24 mm in length, 8-9 mm in width.
*Color (first open, both surfaces).*—4A.
*Color (petals fully expanded).*—Pale cream, between 155A and 2D.

Involucral bracts:
*Quantity.*—Approximately 120 per inflorescence, overlapping, fused at base.
*Bract color (abaxial and adaxial surfaces).*—Ranges between 139C and 138B, except margins 151D.
*Bract length.*—5-8 mm.
*Bract width.*—3 mm.
*Bract apex.*—Rounded with tiny cilia, cilia color 183A.
*Bract base.*—Obtuse.
*Bract surface (both surfaces).*—Glabrous, translucent, waxy towards margins.
*Bract shape.*—Lanceolate.
*Bract margin.*—Entire, smooth, color 151D.

Disc floret:
*Disc diameter.*—3.0 cm.
*Disc floret quantity.*—Approximately 520 per inflorescence, massed at center of receptacle.
*Disc floret dimensions.*—6-7 mm in length, 1 mm in diameter.
*Disc floret shape.*—Tubular.
*Disc floret petal quantity.*—Ranges from 3 to 5 in number, basally fused.
*Disc floret petal dimensions.*—6 mm in length, 0.75 mm-1.0 mm in width.
*Disc floret petal color.*—14A.
*Disc floret petal apex.*—Acute.
*Disc floret petal base.*—Truncate.
*Disc floret corolla tube.*—4 mm in length, 0.75 mm in diameter, color 145B-145C.

Reproductive organs:
*Ray flowers.*—Androecium (stamens, anthers, filaments, pollen): Absent. Pistil: 1, 3 mm in length, hair-like, diameter less than 0.2 mm., color light brown. Stigma: 2 mm in length, forked, branches recurved, diameter less than 0.2 mm, color 145B. Ovary: Not observed.
*Disc flowers.*—General: Stigma, style, and ovary not observed. Stamens: 5, filaments length 3 mm and very fine diameter, color 154C. Anthers, pollen: None observed.

Seed: None observed to date.

COMPARISON WITH PARENTAL LINES AND KNOWN VARIETY

'Real Cream' may be compared with its parents by its foliage and by the color of its ray florets. 'Real Cream' produces distinctly uniformly long, narrow, dentate leaves whereas both parents produce broad leaves with lobes. Whereas the buds and ray florets of 'Real Cream' are yellow and cream-yellow in color, the buds and ray florets of the male parent, L1329-7, are white in color and the buds and ray florets of the female parent, L1402-12, are pale cream in color.

The commercial variety of *Leucanthemum* which the inventor considers to most closely resemble 'Real Cream' is *Leucanthemum* Plant Named 'Leumayel' (U.S. Plant Pat. No. 19,242).

Both 'Real Cream' and 'Leumayel' bear cream-yellow single-type inflorescences. Whereas the inflorescence of 'Real Cream' is comprised mostly of three whorls of ray florets, the inflorescence of 'Leumayel' comprises mostly one whorl and bears many fewer ray florets per inflorescence. In appearance, the inflorescences of 'Real Cream' present distinctly overlapping ray floret petals whereas the inflorescence of 'Leumayel' presents gaps between the ray floret petals.

I claim:

1. A new and distinct cultivar of *Leucanthemum* plant named 'Real Cream' as described and illustrated herein.

* * * * *